United States Patent
Arnaud et al.

(10) Patent No.: US 10,813,854 B2
(45) Date of Patent: Oct. 27, 2020

(54) COMPOSITIONS COMPRISING A SILICONE SURFACTANT, A SILICONE ELASTOMER POWDER AND AN ORGANO-MODIFIED CLAY

(71) Applicant: L'OREAL, Paris (FR)

(72) Inventors: Pascal Arnaud, Les Roses (FR); Valérie Dique-Mouton, Chevilly Larue (FR)

(73) Assignee: L'OREAL, Paris (FR)

( * ) Notice: Subject to any disclaimer, the term of this patent is extended or adjusted under 35 U.S.C. 154(b) by 56 days.

(21) Appl. No.: 15/506,987

(22) PCT Filed: Aug. 26, 2015

(86) PCT No.: PCT/EP2015/069548
§ 371 (c)(1),
(2) Date: Feb. 27, 2017

(87) PCT Pub. No.: WO2016/030420
PCT Pub. Date: Mar. 3, 2016

(65) Prior Publication Data
US 2017/0281479 A1    Oct. 5, 2017

(30) Foreign Application Priority Data

Aug. 28, 2014 (FR) ..................... 14 58081

(51) Int. Cl.
| | | |
|---|---|---|
| *A61K 8/06* | (2006.01) | |
| *A61K 8/894* | (2006.01) | |
| *A61Q 1/12* | (2006.01) | |
| *A61K 8/26* | (2006.01) | |
| *A61K 8/895* | (2006.01) | |

(52) U.S. Cl.
CPC .............. *A61K 8/064* (2013.01); *A61K 8/066* (2013.01); *A61K 8/26* (2013.01); *A61K 8/894* (2013.01); *A61K 8/895* (2013.01); *A61Q 1/12* (2013.01)

(58) Field of Classification Search
CPC .......... A61K 8/064; A61K 8/066; A61K 8/26; A61K 8/894; A61K 8/895; A61Q 1/12
See application file for complete search history.

(56) References Cited

U.S. PATENT DOCUMENTS

2012/0269752 A1* 10/2012 Ozee ..................... A61K 8/042
424/63

FOREIGN PATENT DOCUMENTS

| FR | 2 862 534 A1 | 5/2005 |
| JP | 2000-309509 A | 11/2000 |
| JP | 2002-265317 A | 9/2002 |
| JP | 2014-073974 A | 4/2014 |
| WO | WO-2005/060922 A1 | 7/2005 |

* cited by examiner

*Primary Examiner* — Anna R Falkowitz
(74) *Attorney, Agent, or Firm* — Polsinelli PC

(57) ABSTRACT

This invention relates to a composition in the form of a water-in-oil emulsion that comprises an aqueous phase dispersed in a continuous oily phase, wherein the continuous oily phase comprises:
- at least one organo-modified clay, with a content by weight ranging from 0.5% to 1% relative to the total weight of said composition;
- at least one silicone elastomer powder coated with a silicone resin, with a content by weight ranging from 5% to 12% relative to the total weight of said composition; and
- at least one silicone surfactant with a content by weight ranging from 1.4% to 3% relative to the total weight of said composition;

and wherein the dispersed aqueous phase comprises:
- water at a content by weight ranging from 15% to 25% relative to the total weight of said composition; and
- ethanol at a content by weight ranging from 8% to 18% relative to the total weight of said composition.

13 Claims, No Drawings

COMPOSITIONS COMPRISING A SILICONE SURFACTANT, A SILICONE ELASTOMER POWDER AND AN ORGANO-MODIFIED CLAY

CROSS REFERENCE TO RELATED APPLICATIONS

This application is a National Phase filing under 35 U.S.C. § 371 of PCT/EP2015/069548 filed on Aug. 26, 2015; and this application claims priority to Application No. 14 58081 filed in France on Aug. 28, 2014 under 35 U.S.C. § 119. The entire contents of each application are hereby incorporated by reference.

This invention concerns compositions in the form of a water-in-oil emulsion, comprising a silicone surfactant, a silicone elastomer powder and an organo-modified clay.

This invention also concerns the use of these compositions for makeup or care, in particular of the skin.

Consumers are increasingly looking for cosmetic makeup or skincare products that can be spread in the form of a deposit that should not be thick, but that should blend, on the contrary, as much as possible with the skin.

It is known to a person skilled in the art that very liquid products with a high oil content enable good spreading and skin penetration properties to be obtained.

Mention may be made, as examples of makeup products, of anhydrous liquid foundations, liquid lip gloss, or in the field of skincare products, hydrating oily products and emollients as well as suntan oils.

This very liquid nature can however be at the origin of problems of stability such as sedimentation of pigments, or difficulties for the consumers to use the product, even if the product is proposed in a container that is suited to its fluidity.

In order to overcome this disadvantage, those skilled in the art have tried increasing the viscosity of the product at rest while still desiring to retain its fluidity during application. Oily gelling agents were as such used, such as for example waxes or organo-modified clays, which are known to result in a substantial reduction in the viscosity of the product when it is applied.

However these gelling agents must be used, in order to obtain a substantial gain in viscosity, in proportions that can be detrimental to the optical properties of the deposit by giving it a dull, thick and artificial appearance.

It is therefore still necessary to find a technical solution that can make it possible to increase their gelling properties while retaining for the product spreading properties that are easy and pleasant and a light and natural deposit.

The aim of the invention is therefore to provide a stable composition that has adapted cosmetic properties, in particular intended for makeup or care of the skin.

The aim of the invention is also to provide a composition with high viscosity and that can be used easily in particular for makeup or care of the skin.

This invention also has for purpose to provide a cosmetic composition that is easily applied and which leads to a light and natural deposit.

Thus, this invention relates to a composition in the form of a water-in-oil emulsion that comprises an aqueous phase dispersed in a continuous oily phase, wherein the continuous oily phase comprises:

at least one organo-modified clay, with a content by weight ranging from 0.5% to 1% relative to the total weight of said composition;

at least one silicone elastomer powder coated with a silicone resin, with a content by weight ranging from 5% to 12% relative to the total weight of said composition; and at least one silicone surfactant having the following general formula (I):

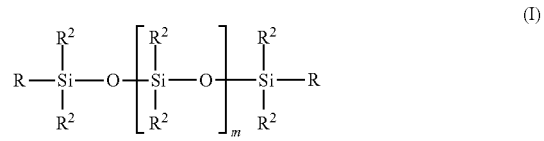

where:

the radicals $R^2$ represent, independently of each other, a $C_1$-$C_3$ alkyl radical or a phenyl radical, m is between 5 and 300, R is a group of formula —$(CH_2)_pO$—$(C_2H_4O)_x(C_3H_6O)_yR^1$ wherein:

$R^1$ represents H, $CH_3$ or $CH_2CH_3$, p is an integer varying from 1 to 5,

X varies from 1 to 100, y varies from 0 to 50, the units $(C_2H_4O)$ and $(C_3H_6O)$ of R being able to be distributed randomly or by blocks, with the content by weight of silicone surfactant being between 1.4% and 3% relative to the total weight of said composition;

and wherein the dispersed aqueous phase comprises:

water at a content by weight ranging from 15% to 25% relative to the total weight of said composition; and ethanol at a content by weight ranging from 8% to 18% relative to the total weight of said composition; said composition having a viscosity at 25° C. ranging from 300 mPa·s to 600 mPa·s.

This invention is based on the association of an organo-modified clay with a silicone elastomer powder coated with a silicone resin, a particular silicone surfactant, water and ethanol in particular proportions that make it possible to obtain, unexpectedly, stable compositions, the viscosity of which is sufficiently high for easy use, which are easily applied and which lead to a light and natural deposit.

According to the invention, the compositions have the form of a water-in-oil emulsion of which the external oily phase contains the organo-modified clay and the silicone elastomer powder coated with a silicone resin.

Without being bound to any theory, the particular silicone surfactant increases the gelling properties of the organo-modified clay in the oily phase, which makes it possible to limit the amount of it.

Viscosity

The compositions of the invention are water-in-oil emulsions of which the viscosity, after one month at rest at ambient temperature (20-25° C.), has a value ranging from 300 mPa·s to 600 mPa·s, and preferable from 320 mPa·s to 400 mPa·s.

When the viscosity is less or greater than this range, the emulsions have a stability over time that is insufficient.

As indicated hereinabove, the measurement of the viscosity is taken after storage of the product, one month at ambient temperature (20-25° C.) then 24 hours in a room maintained at a constant temperature of 20° C.

The viscometer used is a Rheomat 200 from Lamy.

The measurement principle is based on determining the pair required to overcome the resistance of the fluid using an immersed element (moving or measuring body) rotating at a constant speed.

The mobile is chosen in such a way that the measurement is always between 10 and 90 du (integer of deviation units). In the framework of this invention, the moving body 2 (moving ranging from 1 (more fluid) to 5 (thicker)) is generally used.

The product is introduced into a bucket adapted to the moving body chosen and maintained at a temperature of 25° C. using a thermostatically-controlled water bath.

The apparatus is programmed as follows:
Mode: manual
Measurement system: 75 (fixed parameter regardless of the moving body used and programmed by the Lamy company)
Rotation speed: 200 rpm
The reading is taken after 10 minutes of rotation of the moving body.

Organo-Modified Clay

The compositions of the invention contain at least one organo-modified clay which is dispersed in the external oily phase of the emulsion.

In the framework of this invention, the term "organo-modified clay" denotes a clay that is chemically modified by at least one organic group.

The compositions of the invention can contain a organo-modified clay or a mixture of several different organo-modified clays, with regards to the nature of the clay and/or the nature of the chemical modification.

Clays are products that are already well known per se, which are described for example in the work "Minéralogie des argiles, S. Caillère, S. Hénin, M. Rautureau, $2^{nd}$ edition 1982, Masson", of which the teaching is included here as a reference.

As examples of clays that can be used in the composition of the invention, mention may be made of the clays of the kaolinite family such as kaolinite, dickite, nacrite, clays of the halloysite family, dombassite, antigorite, benthierine, pyrophyllite, montmorillonites, beidellite, vermiculites, talc, stevensite, hectorites possibly modified (smectite), saponites, chlorites, sepiolite.

The clay or clays present in the composition of the invention can be natural or synthetic. Natural clay is a sedimentary rock comprised for the most part of specific minerals, silicates in general of aluminum. Kaolin is as such a natural clay.

According to the invention, organo-modified clays are used that are preferably hectorites modified by a C10 to C22 ammonium chloride, and which can, before they are introduced into the composition, have a powdery form or the form of a pre-dispersion in a volatile or non-volatile oil using an activator.

As examples of organo-modified clays in the form of a powder, mention may be made of hectorite modified with distearyldimethylammonium chloride, such as that marketed under the tradename Bentone 38 VCG by ELEMENTIS and hectorite modified by stearylbenzyldimethylammonium chloride, such as that marketed under the tradename Bentone 27 VCG by ELEMENTIS.

As examples of organo-modified clays in the form of a pre-dispersion, mention may be made of the references of the ELEMENTIS company:

- hectorite modified with distearyldimethylammonium chloride, dispersed in cyclopentasiloxane and activated by ethanol, such as that marketed under the tradename Bentone Gel VS 5 V HV,
- hectorite modified with distearyldimethylammonium chloride, dispersed in isododecane and activated by propylene carbonate, such as that marketed under the tradename Bentone Gel ISD V and
- hectorite modified with distearyldimethylammonium chloride, dispersed in isohexadecane and activated by propylene carbonate, such as that marketed under the tradename Bentone Gel IHD V.

According to an embodiment, the compositions according to the invention comprise, as an organo-modified clay, hectorite modified with distearyldimethylammonium chloride, dispersed in isododecane and activated by propylene carbonate.

The organo-modified clay or clays are present at a content ranging from 0.5% to 1.0% by weight in the composition, preferably from 0.55% to 0.8% by weight and even more preferably from 0.6% to 0.7% by weight with respect to the total weight of the composition.

Silicone Elastomer Powder Coated with a Silicone Resin

The compositions of the invention comprise at least one silicone elastomer powder coated with a silicone resin. They can therefore comprise a silicone elastomer powder coated with a silicone resin or a mixture of several different silicone elastomer powders coated with a silicone resin.

According to an embodiment, the silicone elastomer powder is spherical.

'Silicone elastomer' and 'organopolysiloxane elastomer' will be spoken about interchangeably.

The organopolysiloxane elastomer is cross-linked and can be obtained by addition cross-linking reaction of diorganopolysiloxane that contains at least one silicon-bonded hydrogen and diorganopolysiloxane having silicon-bonded ethylenic unsaturated groups, in particular in the presence of a platinum catalyst; or by condensation dehydrogenation cross-linking reaction between a hydroxyl-terminated diorganopolysiloxane and a diorganopolysiloxane that contains at least one silicon-bonded hydrogen, in particular in the presence of an organotin; or by condensation cross-linking reaction of a hydroxyl-terminated diorganopolysiloxane and a hydrolysable organopolysilane; or by thermal cross-linking of organopolysiloxane, in particular in the presence of an organic peroxide catalyst; or by organopolysiloxane cross-linking by high-energy radiation such as gamma rays, ultraviolet rays, electron beams.

Preferably, the elastomer cross-linked organopolysiloxane is obtained by addition cross-linking reaction (A2) of diorganopolysiloxane that contains at least two silicon-bonded hydrogens, and (B2) of diorganopolysiloxane having at least two silicon-bonded ethylenic unsaturated groups, in particular in the presence (C2) of a platinum catalyst, as for example described in application EP 0 295 886.

In particular, the organopolysiloxane can be obtained by reaction of dimethylvinylsiloxy-terminated dimethylpolysiloxane and of trimethylsiloxy-terminated methylhydrogenopolysiloxane, in the presence of a platinum catalyst.

The compound (A2) is the basic reagent for the formation of elastomer organopolysiloxane and the cross-linking takes place via addition reaction of the compound (A2) with the compound (B2) in the presence of the catalyst (C2).

The compound (A2) is advantageously a diorganopolysiloxane that has at least two lower alkenyl groups (for example in C2-C4); the lower alkenyl group can be chosen from the vinyl, allyl, and propenyl groups. These lower alkenyl groups can be located at any position of the organopolysiloxane molecule but are preferably located to the ends of the organopolysiloxane molecule. The organopolysiloxane (A2) can have a branched chain, linear chain, cyclical or network structure but the linear chain structure is preferred. The compound (A2) can have a viscosity ranging from the liquid state to the gum state. Preferably, the compound (A2) has a viscosity of at least 100 centistokes at 25° C.

The organopolysiloxanes (A2) may be chosen from methylvinylsiloxanes, methylvinylsiloxane-dimethylsiloxane copolymers, dimethylvinylsiloxy-terminated dimethylpolysiloxanes, dimethylvinylsiloxy-terminated dim ethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl)polysiloxane, and dimethylvinylsiloxy-terminated dimethylsiloxane-methyl(3,3,3-trifluoropropyl)siloxane copolymers.

The compound (B2) is in particular an organopolysiloxane that has at least 2 silicon-bonded hydrogen atoms in each molecule and is therefore the cross-linker of the compound (A2).

Advantageously, the sum of the number of ethylenic groups per molecule of the compound (A2) and the number of silicon-bonded hydrogen atoms per molecule of the compound (B2) is at least 4.

The compound (B2) can be under any molecular structure, in particular a linear chain, branched chain, cyclical structure.

The compound (B2) can have a viscosity at 25° C. ranging from 1 to 50,000 centistokes, in particular in order to be miscible with the compound (A).

It is advantageous that the compound (B2) be added in a quantity such that the molecular ratio between the total quantity of silicon-bonded hydrogen atoms in the compound (B2) and the total quantity of all of the ethylenic unsaturated groups in the compound (A2) be in the range from 1/1 to 20/1.

The compound (B2) can be chosen from trimethylsiloxy-terminated methylhydrogenopolysiloxanes, trimethylsiloxy-terminated dimethylsiloxane-methylhydrogenosiloxane copolymers, dimethylsiloxane-methylhydrogenosiloxane cyclical polymers.

The compound (C2) is the catalyst of the cross-linking reaction, and is in particular chloroplatinic acid, chloroplatinic-olefin acid complexes, chloroplatinic-alkenylsiloxane acid complexes, chloroplatinic-dicetone acid complexes, black platinum, and supported platinum.

The catalyst (C2) is preferably added from 0.1 to 1000 parts by weight, and better from 1 to 100 parts by weight, as a clean platinum metal for 1000 parts by weight of the total quantity of the compounds (A2) and (B2).

Other organic groups can be silicon bonded in the organopolysiloxane (A2) and (B2) described hereinabove, as for example alkyl groups such as methyl, ethyl, propyl, butyl, octyl; substituted alkyl groups such as 2-phenylethyl, 2-phenylpropyl, 3,3,3-trifluoropropyl; alkyl groups such as phenyl, tolyl, xylyl; substituted aryl groups such as phenylethyl; and substituted monovalent hydrocarbon groups such as an epoxy group, an ester carboxylate group, a mercapto group.

According to a particular embodiment, the composition of the invention comprises at least one elastomer organopolysiloxane powder that does not comprise a phenyl group (referred to as 'non-phenylated').

The composition can further comprise another elastomer organopolysiloxane powder that comprises a phenyl (referred to as 'phenylated'), with preferably a non-phenylated elastomer organopolysiloxane powder/phenylated elastomer organopolysiloxane powder ratio greater than 1.

Advantageously, the Elastomer Organopolysiloxane Powder is Non-Emulsifying.

The term "non-emulsifying" defines organopolysiloxane elastomers that do not contain any hydrophilic chains such as polyoxyalkylene or polyglycerolated patterns.

The silicone elastomer particles are preferably spherical and have an average size that can vary from 0.1 μm to 500 μm, preferably from 3 μm to 200 μm and even better from 10 μm to 20 μm.

According to this invention, the average size of the particles is measured by a particle analyzer and the values obtained are based on the volume and calculated for spherical particles.

They can have a JIS-A hardness that is less than or equal to 80 (in particular ranging from 5 to 80), and preferably less than or equal to 65 (in particular ranging from 5 to 65). The JIS-A hardness measured according to the JIS K 6301 (1995) method established by the Japanese Industrial Standards Committee.

The silicone elastomer powder coated with a silicone resin of the invention are in particular described in applications JP 61-194009, EP 0 242 219, EP 0 295 886 and EP 0 765 656.

The elastomer organopolysiloxane powder is coated with silicone resin.

According to a preferred embodiment, the silicone resin can be a silsesquioxane resin, as described for example in the U.S. Pat. No. 5,538,793.

Such silicone elastomer powders coated with a silicone resin are in particular sold under the trade names KSP 100, KSP 101, KSP 102, KSP 103, KSP 104 and KSP 105 by the company Shin Etsu and have for name INCI "Vinyl dimethicone/methicone silsesquioxane crosspolymer".

The silicone elastomer powder or powders coated with a silicone resin are present at a content ranging from 5% to 12% by weight in the composition, preferably from 6% to 10% by weight and even more preferably from 7% to 9% by weight with respect to the total weight of said composition.

Silicone Surfactant

The compositions of the invention contain at least one silicone surfactant characterized by a chemical structure that contains hydrophilic chains at the two ends (substitution as α-ω) of the main chain of general formula (I) such as defined hereinabove.

They may also comprise a mixture of a several silicone surfactants of the formula (I) as defined above.

In the framework of this application, silicone surfactant or α-ω substituted oxyalkylene silicone will be spoken about interchangeably.

Preferably, the α-ω substituted oxyalkylene silicone used according to this invention has the general formula (I) mentioned hereinabove for which:
all of the radicals $R^2$ are methyl radicals;
p ranges from 2 to 4;
x ranges from 3 to 100; and
m ranges from 50 to 200.

Further preferably, the average molecular weight of the radicals R ranges from 800 to 2,600.

Preferably, the ratio of the weight of the $C_2H_4O$ (x) units to the $C_3H_6O$ (y) units ranges from 100:10 to 20:80. Advantageously, this ratio is about 42/58.

Further preferably, $R^1$ is a methyl group.

Even further preferably, the emulsion according to the invention comprises the α-ω oxyalkylene silicone of the following formula:

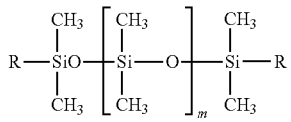

in which:

m=100, $R=(CH_2)_3-O-(C_2H_4O)_x-(C_3H_6O)_y-CH_3$, where x ranges from 3 to 100, y ranges from 1 to 50, with the ratio of the weight of the number of $C_2H_4O$ over the number of $C_3H_6O$ being about 42/58, and the average molecular weight of R ranging from 800 to 1 000.

Among the off-the-shelf products that can contain all or a portion of the α-ω substituted oxyalkylene silicones that can be used according to the invention as an emulsifier, mention may be made in particular of those sold under the trade name of "Abil EM 97" and "Abil EM 97 S" by Evonik Goldschmidt, or "KF 6009", "X22-4350", "X22-4349" or "KF 6008" by Shin-Etsu.

The silicone surfactant or surfactants are present at a content ranging from 1.4% to 3.0% by weight of active material in the composition, preferably from 1.5% to 2.5% by weight and even more preferably from 1.6% to 2.2% by weight with respect to the total weight of the composition.

Aqueous Phase

The compositions of the invention also comprise an aqueous phase that contains at least water at a content ranging from 15% to 25% by weight, and preferably from 17% to 20% by weight, with respect to the total weight of the composition.

The water suitable for the invention can also be a natural spring water or a floral water. In particular, a water suitable for the invention may be a floral water such as cornflower water and/or a mineral water such as VITTEL water, LUCAS water or LA ROCHE POSAY water and/or a spring water.

According to an embodiment, a composition of the invention can further comprise at least one organic solvent miscible in water.

This organic solvent, in particular a solvent, miscible in water, can be chosen from:
  mono-alcohols having 1 to 8 carbon atoms, and in particular 2 to 5 carbon atoms, such as ethanol and isopropanol,
  glycols comprising 2 to 8 carbon atoms, such as propylene glycol, butylene glycol, pentylene glycol, hexylene glycol, dipropylene glycol and caprylylglycol,
  polyethylene glycols,
  polyhydric alcohols having 2 to 8 carbon atoms such as glycerol, and
  mixtures of the latter.

This organic compound, miscible in water, is preferably chosen from glycols in C2-8 such as propylene glycol, butylene glycol, pentylene glycol, hexylene glycol, dipropylene glycol and caprylyl glycol, polyethylene glycols, and polyhydric alcohols in C2-8 such as glycerol.

The aqueous phase can also contain additives chosen from the group consisting of active agents, coloring agents, salts such as sodium chloride and magnesium sulfate, gelling agents, preservatives, and mixtures thereof. It can also comprise any other hydrosoluble additive commonly used in cosmetic products.

According to one embodiment, the aqueous phase represents 23% to 43% by weight, and preferably 27% to 35% by weight, in relation to the total weight of the composition.

Ethanol

The compositions of the invention also comprise, in the aqueous phase, ethanol at a content ranging from 8% to 18% by weight and preferably from 10% to 15% by weight with respect to the total weight of the composition.

Oily Phase

The oily phase (or fat phase) of the compositions according to the invention comprises at least one oil. It may consist of a single oil or a mixture of a plurality of oils. The term "oil" is intended to mean any fatty substance in liquid form at ambient temperature (20-25° C.) and at atmospheric pressure. These oils may be of animal, plant, mineral or synthetic origin.

According to one embodiment, the oily phase represents 21% to 70% by weight, and preferably 40% to 60% by weight, in relation to the total weight of the composition.

According to one embodiment, the oils are chosen from the group consisting of hydrocarbon oils, silicone oils, fluorinated oils and mixtures thereof.

According to the present invention, the term "hydrocarbon oil" denotes an oil containing mainly hydrogen and carbon atoms.

The term "silicone oil" denotes an oil comprising at least one silicon atom and particularly comprising at least one Si—O group.

The term "fluorinated oil" denotes an oil comprising at least one fluorine atom.

The oils may optionally comprise oxygen, nitrogen, sulfur and/or phosphorus atoms, for example in the form of hydroxyl or acid radicals.

According to one embodiment, the oily phase of the compositions according to the invention comprises at least one volatile oil and/or at least one non-volatile oil.

According to one embodiment, the compositions according to the invention comprise 21% to 70%, preferably 40% to 60% by weight of oils with respect to the total weight of said composition.

Volatile Oils

According to one embodiment, the oily phase of the compositions according to the invention comprises at least one volatile oil. The oily phase of the compositions according to the invention may comprise a mixture of several volatile oils.

The term "volatile oil" denotes an oil liable to evaporate on skin contact in less than one hour, at ambient temperature and atmospheric pressure. The volatile oil is a volatile cosmetic oil, liquid at ambient temperature, particularly having a vapor pressure different to zero, at ambient temperature and atmospheric pressure, particularly having a vapor pressure ranging from 0.13 Pa to 40,000 Pa ($10^{-3}$ at 300 mm Hg), and preferably ranging from 1.3 Pa to 13,000 Pa (0.01 to 100 mm Hg), and preferentially ranging from 1.3 Pa to 1,300 Pa (0.01 to 10 mm Hg).

Furthermore, the volatile oil generally has a boiling point, measured at atmospheric pressure, ranging from 150° C. to 260° C. and preferably ranging from 170° C. to 250° C.

The volatile oils may be hydrocarbon, silicone or fluorinated oils.

As a volatile hydrocarbon oil, mention may be made of C8-C16 branched alkanes, such as isoalkanes (also referred to as isoparaffins), isododecane, isohexadecane, and C9-C17 linear alkanes, such as dodecane (C12) and tetradecane (C14), marketed respectively under the references PARAFOL 12-97 and PARAFOL 14-97 by Sasol.

Of the volatile hydrocarbon oils, isododecane is preferred.

According to one embodiment, the compositions according to the invention comprise at least one volatile hydrocarbon oil. Preferably, they comprise at least one C8-C16 branched alkane, and preferably isododecane.

Preferably, the compositions according to the invention comprise 0.1% to 50%, preferably 10% to 25% by weight of volatile hydrocarbon oil(s) with respect to the total weight of the composition.

As a volatile silicone oil, mention may be made of linear or cyclic silicone oils having 2 to 7 silicon atoms, these silicones optionally comprising alkyl or alkoxy groups having 1 to 10 carbon atoms.

As examples, mention may be made of decamethyl cyclopentasiloxane, dodecamethyl cyclohexasiloxane and dodecamethyl pentasiloxane.

Among the volatile silicone oils, dodecamethyl pentasiloxane is preferred.

According to one embodiment, the compositions according to the invention comprise at least one volatile silicone oil. Preferably, they comprise at least dodecamethyl pentasiloxane and or cyclohexasiloxane.

Preferably, the compositions according to the invention comprise 0.1% to 69%, preferably 20% to 35% by weight of volatile silicone oil(s) with respect to the total weight of the composition.

Non-Volatile Oils

According to one embodiment, the oily phase of the compositions according to the invention comprises at least one non-volatile oil. The oily phase of the compositions according to the invention may comprise a mixture of several non-volatile oils.

The term "non-volatile oil" denotes an oil remaining on the skin or keratin fiber at ambient temperature and atmospheric pressure. More specifically, a non-volatile oil has an evaporation rate strictly below 0.01 mg/cm$^2$/min.

To measure this evaporation rate, 15 g of oil or an oil mixture to be tested are introduced into a crystallizer with a diameter of 7 cm, placed on a scale located in a large chamber of around 0.3 m$^3$, with controlled temperature, at 25° C., and hygrometry, at 50% relative humidity. The liquid is left to evaporate freely, without stirring, by allowing ventilation with a fan (PAPST-MOTOREN, reference 8550 N, rotating at 2700 rpm) arranged vertically above the crystallizer containing said oil or said mixture, with the blades being directed toward the crystallizer and at a distance of 20 cm with respect to the crystallizer base. The mass of oil remaining in the crystallizer is measured at regular intervals. The evaporation rates are expressed in mg of oil evaporated per unit of surface (cm$^2$) and per unit of time (minutes).

The non-volatile oils may, in particular, be chosen from non-volatile hydrocarbon, fluorinated and/or silicone oils.

Among the non-volatile hydrocarbon oils, mention can be made of natural oils or oils of natural origin such as paraffin oils or petroleum jelly, plant oils, such as argan oil, blackcurrant oil, sunflower oil, apricot oil, sweet almond oil, jojoba oil and macadamia oil.

Mention can also be made of synthetic oils such as esters such as isodecyl neopentanoate, isononyl isononanoate and octyldodecyl neopentanoate, ethers such as dicapryl ether, or alcohols such as hexyldecanol or octyldodecanol.

Of the non-volatile silicone oils, mention may be made of polydimethylsiloxanes, phenylated silicones such as phenyltrimethicone or alkyldimethicones such as cetyl dimethicone.

Of the non-volatile fluorinated oils, mention may be made of fluorinated silicones and perfluoropolyethers.

According to one embodiment, the compositions according to the invention comprise at least one non-volatile silicone oil. Preferably, they comprise at least dodecamethyl pentasiloxane and or cyclohexasiloxane.

Preferably, the compositions according to the invention comprise 0.1% to 30%, preferably 0.5% to 10% by weight of non-volatile silicone oil(s) with respect to the total weight of the composition.

According to one embodiment, the oily phase comprises at least one oil chosen from the group consisting of volatile hydrocarbon oils, volatile silicone oils, non-volatile silicone oils, and mixtures thereof.

Pigments

The compositions according to the invention may further comprise at least one pigment, in particular a mineral pigment.

They may thus comprise a single mineral pigment or a mixture of a plurality of mineral pigments.

According to one embodiment, the mineral pigment is chosen from the group consisting of metal oxide pigments, composite pigments and mixtures thereof.

Preferably, the mineral pigment is chosen from the group consisting of iron oxides, titanium dioxide, zinc oxides, zirconium oxides, cerium oxides, chromium oxide, manganese violet, ultramarine blue, chromium hydrate, ferric blue and mixtures thereof.

According to a preferred embodiment, the mineral pigment is chosen from titanium dioxide, iron oxides and mixtures thereof. Preferably, the composition according to the invention includes a mixture of titanium oxides and iron oxides.

According to the invention, the compositions of the invention can also comprise a composite pigment, namely a pigment constituted of the association of one or a plurality of mineral pigments with one or a plurality of mineral or organic fillers.

According to one embodiment, the composite pigment is chosen from the group consisting of iron or titanium oxides coated with silica or alumina, iron or titanium oxides coated with organic compounds such as cellulose, pigments resulting from the coating of a silica bead with iron or titanium oxides, and mixtures thereof.

Preferably, the content in pigment(s) is between 0.1% and 20%, preferably between 5.0% and 15.0%, by weight in relation to the total weight of the composition.

According to a preferred embodiment, the cosmetic compositions according to the invention comprise pigment particle(s) coated with a lipophilic compound, these particles may be identical or different. The compositions according to the invention may thus comprise mixtures of pigment particles of different types.

The particle size of the pigment is strictly greater than 100 nm.

According to the invention, the term "size" of a particle denotes the D50 thereof. The D50, or median size by volume, corresponds to the particle size defined such that 50% by volume of the particles have a size less than D50.

The median size by volume may be assessed by means of light diffraction using a Malvern MasterSizer laser granulometer, said particles under evaluation being dispersed in a liquid medium such as for example octyldodecyl neopentanoate.

According to one embodiment, the size of the pigment(s) particles according to the invention ranges from 100 nm to 25 µm, preferably from 200 nm to 10 µm.

The pigments are coated hydrophobically so as to be situated in the oily phase of the emulsion, i.e. in the external phase.

Preferably, the composition comprises at least inorganic pigments coated with at least one lipophilic compound, particularly at least titanium oxide and iron oxides coated with at least one lipophilic compound.

According to the invention, the coating of a pigment according to the invention generally denotes the full or partial surface treatment of the pigment by a surface agent, absorbed, adsorbed or grafted onto said pigment.

The coating of the pigment particles according to the invention may be partial or full. Within the scope of this invention, the term "partially coated" denotes that the pigment is coated with at least one layer of coating at a rate of 50% to 99.9% of the surface of said pigment.

According to the invention, the coating of the pigments may comprise one or a plurality of lipophilic compounds, and optionally also one or a plurality of non-lipophilic compounds.

The surface-treated pigments may be prepared using chemical, electronic, mechano-chemical or mechanical surface treatment techniques well known to those skilled in the art. Commercial products may also be used.

The surface agent may be absorbed, adsorbed or grafted onto the pigments by means of solvent evaporation, chemical reaction or creation of a covalent bond.

According to one alternative embodiment, the surface treatment consists of a solid particle coating.

The coating may represent 0.1% to 20% by weight and particularly 0.5% to 5% by weight of the total weight of the coated pigment.

The coating may be carried out for example by adsorbing a liquid surface agent on the surface of the solid particles merely by mixing while stirring the particles and said surface agent, optionally heated, before incorporating the particles in the other ingredients of the makeup or treatment composition.

The coating may be carried out for example by means of a chemical reaction of a surface agent with the surface of the solid pigment particles and the creation of a covalent bond between the surface agent and the particles. This method is particularly described in the U.S. Pat. No. 4,578,266.

The chemical surface treatment may consist of diluting the surface agent in a volatile solvent, dispersing the pigments in this mixture, and then slowly evaporating the volatile solvent, such that the surface agent is deposited on the surface of the pigments.

Lipophilic or Hydrophobic Treatment Agent

According to one particular embodiment of the invention, the pigments may be coated according to the invention with at least one lipophilic compound chosen from the group consisting of silicone surface agents, fluorinated surface agents, fluorosilicone surface agents, metallic soaps, N-acylated amino acids and salts thereof, lecithin and derivatives thereof, isopropyl triisostearyl titanate, isostearyl sebacate, plant or animal natural waxes, polar synthetic waxes, fatty esters, phospholipids and mixtures thereof.

Silicone Surface Agent

According to one particular embodiment, the pigments may be fully or partially surface-treated with a silicone compound.

The silicone surface agents may be chosen from organopolysiloxanes, silane derivatives, silicon-acrylate copolymers, silicone resins, and mixtures thereof.

The term organopolysiloxane denotes a compound having a structure comprising an alternation of silicon atoms and oxygen atoms and comprising organic radicals bound with silicon atoms.

As examples of pigments treated with a silicone compound, mention may be made of the following pigments treated with:

Triethoxycaprylylsilane treatment such as the AS surface treatment (LCW) and the OTS surface treatment (Daito);

Methicone treatment such as the SI surface treatment (LCW);

Dimethicone treatment such as the Covasil 3.05 (LCW) or SA (Miyoshi) or SI01 (Daito) surface treatment Dimethicone/Trimethylsiloxysilicate treatment such as the Covasil 4.05 surface treatment (LCW); and Acrylate Copolymer/Dimethicone treatment such as the ASC surface treatment (Daito).

Fluorinated Surface Agent

The pigments may be fully or partially surface-treated with a fluorinated compound.

The fluorinated surface agents may be chosen from perfluoroalkyl phosphates, perfluoropolyethers, polytetrafluoropolyethylene (PTFE), perfluoroalkanes, perfluoroalkyl silazanes, hexafluoropropylene polyoxides or polyorganosiloxanes comprising perfluoroalkyl perfluoropolyether groups.

As examples of commercial pigments treated with a fluorinated compound, mention may be made of the following pigments treated with:

Perfluoropolymethylisopropyl ether treatment such as the FHC surface treatment (LCW); and Perfluoroalkyl Phosphate treatment such as the PF surface treatment (Daito).

Fluorosilicone Surface Agent

The pigments may be fully or partially surface-treated with a fluorosilicone compound.

The fluorosilicone compound may be chosen from perfluoroalkyl dimethicones, perfluoroalkyl silanes and perfluoroalkyl trialkoxysilanes.

As examples of commercial pigments treated with a fluorosilicone compound, mention may be made of the following pigments subjected to the following treatments:

Acrylate Copolymer/Dimethicone and Perfluoroalkyl Phosphate treatment such as the FSA surface treatment (Daito).

Polymethyl hydrogen siloxane/Perfluoroalkyl Phosphate treatment such as the FS01 surface treatment (Daito);

Octyltriethylsilane/Perfluoroalkyl Phosphate treatment such as the FOTS surface treatment (Daito); and Perfluorooctyl Triethoxysilane treatment such as the FHS surface treatment (Daito).

Other Lipophilic Surface Agents

The hydrophobic treatment agent may also be chosen from metallic soaps such as aluminum dimyristate, the aluminum salt of hydrogenated tallow glutamate.

As metallic soaps, mention may particularly be made of metallic soaps of fatty acids having 12 to 22 carbon atoms, and particularly those having 12 to 18 carbon atoms.

The metal of the metallic soap may particularly be zinc or magnesium. As a metallic soap, zinc laurate, magnesium stearate, magnesium myristate, zinc stearate, and mixtures thereof may be used.

The fatty acid may particularly be chosen from lauric acid, myristic acid, stearic acid and palmitic acid.

The hydrophobic treatment agent may also be chosen from N-acylated amino acids or salts thereof which may comprise an acyl group having 8 to 22 carbon atoms, such as for example a 2-ethylhexanoyl, caproyl, lauroyl, myristoyl, palmitoyl, stearoyl or cocoyl group.

The amino acid may be for example lysine, glutamic acid or alanine.

The salts of these compounds may be aluminum, magnesium, calcium, zirconium, zinc, sodium or potassium salts.

In this way, according to one particularly preferred embodiment, an N-acylated amino acid derivative may be particularly a glutamic acid derivative and/or any of the salts thereof, and more particularly a stearoyl glutamate, such as for example aluminum stearoyl glutamate.

According to one preferred embodiment, the cosmetic composition according to the invention comprises pigment particles obtained by treating with aluminum stearoyl glutamate. In particular, the cosmetic composition may comprise iron and/or titanium oxides coated with aluminum stearoyl glutamate.

The hydrophobic treatment agent may also be chosen from:
  lecithin and derivatives thereof,
  isopropyl triisostearyl titanate,
  isostearyl sebacate,
  plant or animal natural waxes or polar synthetic waxes,
  fatty esters, particularly with jojoba esters,
  phospholipids, and
  mixtures thereof.

As examples of commercial pigments treated with compounds as defined above, mention may be made for example of pigments subjected to the following treatments:
  Lauroyl Lysine treatment such as the LL surface treatment (LCW);
  Lauroyl Lysine Dimethicone treatment such as the LL/SI surface treatment (LCW);
  Magnesium Myristate treatment such as the MM surface treatment (LCW);
  Magnesium Stearate treatment such as the MST surface treatment (Daito).
  Hydrogenated Lecithin treatment such as the HLC surface treatment (LCW);
  Aluminum Dimyristate treatment such as the MI surface treatment (Miyoshi);
  Isostearyl Sebacate treatment such as the HS surface treatment (Miyoshi);
  Disodium Stearoyl Glutamate treatment such as the NAI surface treatment (Miyoshi);
  Sodium Dilauramidoglutamide lysine treatment such as the ASL surface treatment (Daito);
  Dimethicone/Disodium Stearoyl Glutamate treatment such as the SA/NAI surface treatment (Miyoshi);
  Hydrogenated Stearyl Olive Esters treatment such as the MiyoNAT surface treatment (Miyoshi);
  Lauroyl Lysine/Aluminum Tristearate treatment such as the LL-StAl surface treatment (Daito);
  Isopropyl Titanium Triisostearate treatment such as the ITT surface treatment (Daito); or
  Perfluoroalkyl Phosphate/Isopropyl Titanium Triisostearate treatment such as the PF+ITT surface treatment (Daito).

The pigments coated according to the invention with at least one lipophilic compound, may be present in a composition according to the invention at a concentration ranging from 0.1% to 20% by weight, in relation to the total weight of the composition, preferably 5% to 15% by weight.

Additives

A cosmetic composition according to the invention may also further comprise any additive normally used in the field in question, for example selected from anionic, cationic, amphoteric or nonionic surfactants, silicone surfactants, hydrophilic or lipophilic gelling agents, gums, resins, dispersants, film-forming polymers organic or mineral fillers, coloring agents such as nacres, hydrosoluble and liposoluble coloring agents, antioxidants, essential oils, preservatives, salts, perfumes, neutralizing agents, antiseptics, anti-UV protective agents, cosmetic agents, such as vitamins, hydrating agents such as glycerol, emollients or collagen-protecting agents, and mixtures thereof.

A person skilled in the art can adjust the type and quantity of additives present in the compositions according to the invention by means of routine operations, so that the cosmetic properties and the stability properties sought for these compositions are not affected by the additives.

According to one embodiment, the oily phase of the compositions according to the invention further comprises at least one lipophilic chemical filter.

As examples of lipophilic chemical filters, mention can for example be made of Homosalate, Ethylhexyl Salicylate, Ethylhexyl Methoxycinnamate, Octocrylene, Butyl Methoxydibenzoylmethane, Ethylhexyl triazone, Diethylhexyl Butamido Triazone and Drometrizole Trisiloxane.

According to a particular embodiment, the compositions of the invention comprise ethylhexyl methoxycinnamate as a lipophilic chemical filter.

According to one embodiment, the content in lipophilic chemical filter ranges from 0.01% to 15% by weight, and preferably 1.0% to 10% by weight in relation to the total weight of the composition.

Cosmetic Compositions

The present invention also relates to a cosmetic composition including, in a physiologically acceptable medium, a composition such as defined above.

The term "physiologically acceptable medium" is intended to denote a medium that is particularly suitable for the application of a composition of the invention to the skin or the lips.

The physiologically acceptable medium is generally suitable for the nature of the support to which the composition should be applied, and also for the way in which the composition is to be packaged.

Applications

The present invention also relates to a non-therapeutic cosmetic method for coating with keratin materials, in particular the skin, including a step for applying on said keratin materials, in particular the skin, of at least one layer of a cosmetic composition as defined hereinabove.

The invention also relates to a non-therapeutic cosmetic care and/or makeup for the skin, including a step for applying on the skin of at least one layer of a cosmetic composition as defined hereinabove.

The cosmetic compositions according to the invention may be face or body treatment or makeup products. In particular, they can be in the form of a foundation.

These compositions of the invention are thus intended in particular to be applied onto the skin.

Throughout the application, the term "comprising a" or "including a" means "comprising at least one" or "including at least one", unless otherwise specified.

Throughout the above description, unless specified otherwise, the term "between x and y" refers to an inclusive range, i.e. the values x and y are included in the range.

EXAMPLES

Examples 1 to 3: Influence of the Nature of the Surfactant on Stability

The examples of foundation 1 to 3 make it possible to show the superiority of the silicone surfactant of the invention with formula (I) with respect to two other silicone surfactants of different structures.

Phase A2 is prepared separately by grinding three times, in a three-roll mill, the mixture of pigments and cyclohexasiloxane.

This phase A2 is then added into the main beaker while stirring using a Moritz mixer (700 to 800 rpm) for 30 minutes at ambient temperature.

Then the phase B1 is added under stirring in the Moritz (1000-1200 rpm) for 10 minutes, and the phase B2 by maintaining the stirring for 5 minutes.

Finally the phase C is introduced by stirring in the Moritz (1500-1600 rpm) for 10 minutes.

|  |  | Example 1 (Invention) mass % | Example 2 (Comparative) mass % | Example 3 (Comparative) mass % |
|---|---|---|---|---|
| A1 | Bis-PEG/PPG-14/14 Dimethicone/Dimethicone (85/15) sold under the reference Abil EM 97 S by Evonik Goldschmidt | 2.00 (1.70 MA) | — | — |
|  | PEG 10 dimethicone sold under the reference KF 6017 by Shin-Etsu | — | 1.70 | — |
|  | PEG 9 polydimethylsiloxyethyl dimethicone sold under the reference KF 6028 by Shin-Etsu | — | — | 1.70 |
|  | Dimethicone (5 cSt) | — | 0.30 | 0.30 |
|  | Isododecane | 11.00 | 11.00 | 11.00 |
|  | Phenyltrimethicone sold under the reference DC 556 by Dow Corning | 2.00 | 2.00 | 2.00 |
|  | Ethyl hexyl methoxycinnamate | 3.00 | 3.00 | 3.00 |
|  | Dodecamethylpentasiloxane | 8.51 | 8.51 | 8.51 |
|  | Cyclohexasiloxane | 12.10 | 12.10 | 12.10 |
|  | Vinyl dimethicone/Methicone Silsesquioxane cross-polymer sold under the reference KSP 100 by Shin Etsu | 8.00 | 8.00 | 8.00 |
| A2 | Cyclohexasiloxane | 4.00 | 4.00 | 4.00 |
|  | Titanium dioxide coated with aluminum stearoyl glutamate sold under the reference NAI-TAO-77891 by Miyoshi Kasei | 10.04 | 10.04 | 10.04 |
|  | Yellow iron oxide coated with aluminum stearoyl glutamate (3%) sold under the reference NAI-C33-9001-10 by Miyoshi Kasei | 1.72 | 1.72 | 1.72 |
|  | Red iron oxide coated with aluminum stearoyl glutamate (3%) sold under the reference NAI-C33-8001-10 by Miyoshi Kasei | 0.33 | 0.33 | 0.33 |
|  | Black iron oxide coated with aluminum stearoyl glutamate (3%) sold under the reference NAI-C33-7001-10 by Miyoshi Kasei | 0.13 | 0.13 | 0.13 |
| B1 | Demineralized water | 19.17 | 19.17 | 19.17 |
| B2 | Denatured ethanol at 96° | 12.00 | 12.00 | 12.00 |
| C | Disteardimonium hectorite/propylene carbonate/isododecane (10/3/87) sold under the reference BENTONE GEL ISD V by Elementis | 6.00 (0.6% MA) | 6.00 (0.6% MA) | 6.00 (0.6% MA) |
|  | TOTAL | 100% | 100% | 100% |

Procedure

The constituents of phase A1 are weighed in the main beaker and stirred, at an ambient temperature using a Moritz mixer (600 to 700 rpm) for 15 minutes until homogenization.

Stability

The stability of the product is evaluated visually, after storing for two months at 4, 25, 37 and 45° C.

Viscosity is measured according to the method described hereinabove in the description.

|  | Example 1 (Invention) | Example 2 (comparative) | Example 3 (comparative) |
|---|---|---|---|
| Viscosity 1 month Tamb (mPa · s) | 350 | 262 | 230 |
| Stability | Good stability The product has a homogeneous fluid aspect, a very light oily film is observed on the surface at all temperatures. | Poor stability Exudation of oil on the surface at all temperatures and the start of flocculation at ambient temperature (consistency of the product is not homogeneous). | Poor stability Slight exudation of oil on the surface at all temperatures and the start of flocculation at ambient temperature (consistency of the product is not homogeneous). |

It was therefore observed that the silicone surfactant according to the invention makes it possible to obtain cosmetic compositions with satisfactory properties, in particular in terms of stability. Such properties are not however obtained by using other silicone surfactants in light of the results obtained for the comparative examples 2 and 3.

Examples 4 and 5: Influence of the Rates of the Constituents on Stability

Example 4 (comparative) of foundation makes it possible to show that when the rate of surfactant of the invention in active material is less than the low value of the range according to the invention (1.4%), stability is insufficient.

Example 5 (comparative) of foundation makes it possible to show that when the rate of organo-modified clay is higher than the high value of the range according to the invention (1.0%) and when the rate of water is less than the low value of the range according to the invention (15%), stability is insufficient.

|    |                                                                                                                   | Example 4 (Comparative) mass % | Example 5 (Comparative) mass % |
|----|-------------------------------------------------------------------------------------------------------------------|--------------------------------|--------------------------------|
| A1 | Bis-PEG/PPG-14/14 Dimethicone/Dimethicone (85/15) sold under the reference Abil EM 97 S by Evonik Goldschmidt     | 1.50 (1.28 MA)                 | 2.00 (1.70 MA)                 |
|    | Isododecane                                                                                                        | 7.00                           | 7.00                           |
|    | Phenyltrimethicone sold under the reference DC 556 □by Dow Corning                                                 | 2.00                           | 2.00                           |
|    | Ethyl hexyl methoxycinnamate                                                                                       | 3.00                           | 3.00                           |
|    | Dodecamethylpentasiloxane                                                                                          | 10.51                          | 25.61                          |
|    | Cyclohexasiloxane                                                                                                  | 16.60                          | 2.00                           |
|    | Vinyl dimethicone/Methicone Silsesquioxane cross-polymer sold under the reference KSP 100 by Shin Etsu             | 7.00                           | 8.00                           |
| A2 | Cyclohexasiloxane                                                                                                  | 4.00                           | 4.00                           |
|    | Titanium dioxide coated with aluminum stearoyl glutamate sold under the reference NAI-TAO-77891 by Miyoshi Kasei   | 10.04                          | 10.04                          |
|    | Yellow iron oxide coated with aluminum stearoyl glutamate (3%) sold under the reference NAI-C33-9001-10 by Miyoshi Kasei | 1.72                     | 1.72                           |
|    | Red iron oxide coated with aluminum stearoyl glutamate (3%) sold under the reference NAI-C33-8001-10 by Miyoshi Kasei | 0.33                        | 0.33                           |
|    | Black iron oxide coated with aluminum stearoyl glutamate (3%) sold under the reference NAI-C33-7001-10 by Miyoshi Kasei | 0.13                      | 0.13                           |
| B1 | Demineralized water                                                                                                | 16.17                          | 14.17                          |
| B2 | Denatured ethanol at 96°                                                                                           | 10.00                          | 8.00                           |
| C  | Disteardimonium hectorite/propylene carbonate/isododecane (10/3/87) sold under the reference BENTONE GEL ISD V by Elementis | 10.00 (1.0% MA)         | 12.00 (1.2% MA)                |
|    | TOTAL                                                                                                              | 100%                           | 100%                           |

The compositions of the examples 4 and 5 were prepared according to the operating procedure described in examples 1 and 2.

Viscosity and Stability

Viscosity is measured according to the method described hereinabove in the description.

|                              | Example 4 (comparative)                                                                   | Example 5 (comparative)                                                                  |
|------------------------------|-------------------------------------------------------------------------------------------|------------------------------------------------------------------------------------------|
| Viscosity 1 month Tamb (mPa · s) | 540                                                                                   | 650                                                                                      |
| Stability                    | Poor stability Start of flocculation (cracks) and exudation of oil on the surface at all temperatures. | Poor stability Flocculation (cracks) and exudation of oil on the surface at all temperatures. |

The results obtained made it possible to show that the compositions of the examples 4 and 5 were not stable and therefore did not have satisfactory properties.

Example 6: Influence of Viscosity on Stability

Example 6 (comparative) of foundation makes it possible to show that when the viscosity is less than the low value of the range according to the invention (300 mPa·s.), stability is insufficient.

|   |   | Example 6 (Comparative) mass % |
|---|---|---|
| A1 | Bis-PEG/PPG-14/14 Dimethicone/Dimethicone (85/15) sold under the reference Abil EM 97 S by Evonik Goldschmidt | 2.00 (1.70 MA) |
|   | Isododecane | 12.00 |
|   | Phenyltrimethicone sold under the reference DC 556 ☐by Dow Corning | 2.00 |
|   | Ethyl hexyl methoxycinnamate | 3.00 |
|   | Dodecamethylpentasiloxane | 8.51 |
|   | Cyclohexasiloxane | 12.10 |
|   | Vinyl dimethicone/Methicone Silsesquioxane cross-polymer sold under the reference KSP 100 by Shin Etsu | 8.00 |
| A2 | Cyclohexasiloxane | 4.00 |
|   | Titanium dioxide coated with aluminum stearoyl glutamate sold under the reference NAI-TAO-77891 by Miyoshi Kasei | 10.04 |
|   | Yellow iron oxide coated with aluminum stearoyl glutamate (3%) sold under the reference NAI-C33-9001-10 by Miyoshi Kasei | 1.72 |
|   | Red iron oxide coated with aluminum stearoyl glutamate (3%) sold under the reference NAI-C33-8001-10 by Miyoshi Kasei | 0.33 |
|   | Black iron oxide coated with aluminum stearoyl glutamate (3%) sold under the reference NAI-C33-7001-10 by Miyoshi Kasei | 0.13 |
| B1 | Demineralized water | 19.17 |
| B2 | Denatured ethanol at 96° | 12.00 |
| C | Disteardimonium hectorite/propylene carbonate/isododecane (10/3/87) sold under the reference BENTONE GEL ISD V by Elementis | 5.00 (0.5% MA) |
|   | TOTAL | 100% |

The composition of the example 6 was prepared according to the operating procedure described in examples 1 and 2.

Viscosity and Stability

Viscosity is measured according to the method described hereinabove in the description.

|   | Example 6 (Comparative) |
|---|---|
| Viscosity 1 month Tamb (mPa · s) | 278 |
| Stability | Poor stability Presence of an oily film on the surface of the product at all temperatures and more substantial sedimentation at 45° C. |

Examples 7 to 9: Compositions According to the Invention

Examples 7 to 9 make it possible to illustrate the invention through different percentages of ingredients of the association.

|   |   | Example 7 (Invention) mass % | Example 8 (Invention) mass % | Example 9 (Invention) mass % |
|---|---|---|---|---|
| A1 | Bis-PEG/PPG-14/14 Dimethicone/Dimethicone (85/15) sold under the reference Abil EM 97 S by Evonik Goldschmidt | 2.00 (1.70 MA) | 2.00 (1.70 MA) | 2.00 (1.70 MA) |
|   | Isododecane | 10.00 | 9.00 | 7.00 |
|   | Phenyltrimethicone sold under the reference DC 556 by Dow Corning | 2.00 | 2.00 | 2.00 |
|   | Ethyl hexyl methoxycinnamate | 3.00 | 3.00 | 3.00 |
|   | Dodecamethylpentasiloxane | 8.51 | 8.51 | 11.01 |

-continued

|  |  | Example 7 (Invention) mass % | Example 8 (Invention) mass % | Example 9 (Invention) mass % |
|---|---|---|---|---|
|  | Cyclohexasiloxane | 12.10 | 12.10 | 16.60 |
|  | Vinyl dimethicone/Methicone Silsesquioxane cross-polymer sold under the reference KSP 100 by Shin Etsu | 8.00 | 8.00 | 8.00 |
| A2 | Cyclohexasiloxane | 4.00 | 4.00 | 4.00 |
|  | Titanium dioxide coated with aluminum stearoyl glutamate sold under the reference NAI-TAO-77891 by Miyoshi Kasei | 10.04 | 10.04 | 10.04 |
|  | Yellow iron oxide coated with aluminum stearoyl glutamate (3%) sold under the reference NAI-C33-9001-10 by Miyoshi Kasei | 1.72 | 1.72 | 1.72 |
|  | Red iron oxide coated with aluminum stearoyl glutamate (3%) sold under the reference NAI-C33-8001-10 by Miyoshi Kasei | 0.33 | 0.33 | 0.33 |
|  | Black iron oxide coated with aluminum stearoyl glutamate (3%) sold under the reference NAI-C33-7001-10 by Miyoshi Kasei | 0.13 | 0.13 | 0.13 |
| B1 | Demineralized water | 19.17 | 19.17 | 16.17 |
| B2 | Denatured ethanol at 96° | 12.00 | 12.00 | 8.00 |
| C | Disteardimonium hectorite/propylene carbonate/isododecane (10/3/87) sold under the reference BENTONE GEL ISD V by Elementis | 7.00 (0.7% MA) | 8.00 (0.8% MA) | 10.00 (1.0% MA) |
|  | TOTAL | 100% | 100% | 100% |

The compositions of the examples 7 to 9 were prepared according to the operating procedure described in examples 1 and 2.

Viscosity and Stability

Viscosity is measured according to the method described hereinabove in the description.

|  | Example 7 (Invention) | Example 8 (Invention) | Example 9 (Invention) |
|---|---|---|---|
| Viscosity 1 month Tamb (mPa · s) | 383 | 500 | 500 |
| Stability | Good stability The product has a smooth and homogeneous aspect at 25° C., tiny traces of oil are observed at the other temperatures. | Good stability The aspect of the product is slightly thicker at 25° C. | Good stability The product has a smooth aspect. A very thin oily film is observed at all temperatures. |

These results have made it possible to demonstrate that the compositions according to the invention are stable and have satisfactory properties.

The invention claimed is:

1. A composition in the form of a water-in-oil emulsion that comprises an aqueous phase dispersed in a continuous oily phase, wherein the continuous oily phase comprises:

a hectorite modified by distearyldimethylammonium in isododecane and activated by propylene carbonate, with a content by weight ranging from 0.5% to 1% relative to the total weight of said composition;

at least one silicone elastomer powder coated with a silicone resin wherein the silicone resin is a silsesquioxane resin having INCI name: Vinyl dimethicone/methicone silsesquioxane crosspolymer, with a content by weight ranging from 5% to 12% relative to the total weight of said composition; and at least one silicone surfactant having the following general formula (I):

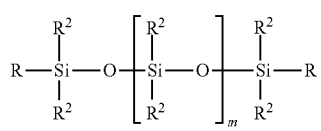

where:
the radicals $R^2$ represent independently of each other, a $C_1$-$C_3$ alkyl radical or a phenyl radical,
m=100,
R=$(CH_2)_3$—O—$(C_2H_4O)_x$—$(C_3H_6O)_y$—$CH_3$,
where x ranges from 3 to 100, y ranges from 1 to 50, with the ratio of the weight of the number of $C_2H_4O$ over the number of $C_3H6O$ being about 42/58, and the average molecular weight of R ranging from 800 to 1 000,
with the content by weight of the at least one silicone surfactant being between 1.6% and 2.2% relative to the total weight of said composition,
from 10% to 25% by weight of isododecane,
from 20% to 35% by weight of a mixture of dodecamethyl pentasiloxane and cyclohexasiloxane,
from 0.5% to 10% by weight phenyltrimethicone;
and wherein the dispersed aqueous phase comprises:
water at a content by weight ranging from 15% to 25% relative to the total weight of said composition; and
ethanol at a content by weight ranging from 8% to 18% relative to the total weight of said composition;
said composition having a viscosity at 25° C. ranging from 300 mPa·s to 600 mPa·s.

2. The composition according to claim 1, wherein the at least one silicone surfactant has the following general formula:

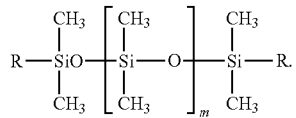

3. The composition according to claim 1, wherein the silicone elastomer powder is in the form of spherical particles with an average size ranging from 0.1 μm to 500 μm.

4. The composition according to claim 1, further comprising at least one oil chosen from the group consisting of hydrocarbon oils, silicone oils, fluorinated oils and mixtures thereof.

5. The composition according to claim 1, further comprising at least one pigment.

6. The composition according to claim 1, further comprising particles of iron coated with aluminum stearoyl glutamate and/or titanium oxides coated with aluminum stearoyl glutamate.

7. The composition according to claim 1, wherein the oily phase further comprises at least one lipophilic chemical filter.

8. The composition according to claim 1, wherein the aqueous phase further comprises additives chosen from the group consisting of active agents, coloring agents, salts, gelling agents, preservatives and mixtures thereof.

9. A cosmetic composition comprising, in a physiologically acceptable medium, a composition according to claim 1.

10. A non-therapeutic cosmetic method for coating with keratin materials, in particular the skin, including a step for applying on said keratin materials, in particular the skin, of at least one layer of a cosmetic composition according to claim 9.

11. A non-therapeutic cosmetic care and/or makeup for the skin comprising the composition of claim 9.

12. The composition according to claim 1, wherein the hectorite modified by distearyldimethylammonium in isododecane and activated by propylene carbonate is present at a content by weight ranging from 0.7% to 1% relative to the total weight of said composition.

13. The composition according to claim 1, wherein at least one silicone elastomer powder coated with a silicone resin is present at a content by weight ranging from 7% to 9% relative to the total weight of said composition.

* * * * *